United States Patent
Franklin et al.

(10) Patent No.: US 6,264,931 B1
(45) Date of Patent: Jul. 24, 2001

(54) HAIR CONDITIONER AND 2 IN 1 CONDITIONING SHAMPOO

(75) Inventors: Ralph Franklin, Danbury, CT (US); Paul Iacobucci, Patterson, NY (US); Dale Steichen, Danbury, CT (US); Diana Tang, Albertson; Phuong-Nga Trinh, Dobbs Ferry, both of NY (US)

(73) Assignee: Akzo Nobel nv., Arnhem (NL)

( * ) Notice: Subject to any disclaimer, the term of this patent is extended or adjusted under 35 U.S.C. 154(b) by 0 days.

(21) Appl. No.: 09/309,255

(22) Filed: May 10, 1999

Related U.S. Application Data

(62) Division of application No. 08/910,281, filed on Aug. 13, 1997, now Pat. No. 5,939,059.

(51) Int. Cl.⁷ .............................. A61K 7/08; A61K 7/075
(52) U.S. Cl. ..................... 424/70.19; 424/70.22; 424/70.27; 424/70.28; 510/119; 510/124; 510/129
(58) Field of Search ................ 424/401, 70.27, 424/70.28, 70.19, 70.22; 510/119, 124, 129

(56) References Cited

U.S. PATENT DOCUMENTS

| | | |
|---|---|---|
| 3,632,396 | 1/1972 | Perez-Zamora . |
| 4,370,272 | 1/1983 | Wechsler et al. . |
| 4,675,131 | 6/1987 | Walraevens et al. . |
| 4,767,547 | 8/1988 | Straathof et al. . |
| 4,938,953 | 7/1990 | Pena et al. . |
| 5,034,218 | 7/1991 | Duvel . |
| 5,106,613 | 4/1992 | Hartnett et al. . |
| 5,145,607 | 9/1992 | Rich . |
| 5,358,667 | 10/1994 | Bergmann . |
| 5,384,114 | 1/1995 | Dowell et al. . |
| 5,411,729 | 5/1995 | O'Lenick, Jr. . |
| 5,552,018 | 9/1996 | Devenyns . |
| 5,552,089 | 9/1996 | Misselyn et al. . |
| 5,552,137 | 9/1996 | Manning et al. . |
| 5,679,331 | 10/1997 | Hague et al. . |
| 5,886,201 | * 3/1999 | Bonastre et al. . |

FOREIGN PATENT DOCUMENTS

| | | |
|---|---|---|
| 0208533 | 1/1987 | (EP) . |
| 0255604 | 2/1988 | (EP) . |
| 0636356 | 2/1995 | (EP) . |
| 0655236 | 5/1995 | (EP) . |
| 0707059 | 4/1996 | (EP) . |
| 2324290 | 4/1977 | (FR) . |
| 5163218 | 6/1993 | (JP) . |
| 5163219 | 6/1993 | (JP) . |
| 9210163 | 6/1992 | (WO) . |

OTHER PUBLICATIONS

Chemical Abstracts 121:282708.
Chemical Abstracts 110:195197.

* cited by examiner

*Primary Examiner*—Thurman K. Page
*Assistant Examiner*—Brian K. Seidleck
(74) *Attorney, Agent, or Firm*—Dilworth & Barrese, LLP

(57) ABSTRACT

A 2-in-1 conditioning shampoo includes an anionic surfactant and a cationic hair conditioning agent. The cationic hair conditioning agent is a fatty aliphatic quaternary ammonium compound having ester linkages. The cationic hair conditioning agent can be prepared by reacting an alkanol amine with a fatty acid or fatty acid ester having an aliphatic group of from about 11 to about 24 carbon atoms and thereafter quaternizing the resulting esteramine with an alkylating agent.

10 Claims, No Drawings

HAIR CONDITIONER AND 2 IN 1 CONDITIONING SHAMPOO

This is a divisional of U.S. application Ser. No. 08/910,281 filed Aug. 13, 1997, now U.S. Pat. No. 5,939,059.

BACKGROUND

1. Technical Field

The present disclosure relates to hair conditioners and 2-in-1 conditioning shampoos.

2. Background of Related Art

Hair conditioners are widely known and used to impart desirable attributes to human hair. For example, hair treated with conditioners is noticeably smoother and softer to the touch. Additionally, hair conditioners render the hair more rinsable and impart a greater ease of detangling and greater manageability to combing, brushing, and styling.

Cationic surfactants and quaternary ammonium compounds have been used in personal care products to improve the appearance, feeling and health of the treated hair. Cationic surfactants are those in which the surfactant activity resides in the positively charged cation portion of the molecule. The cationic surfactants are therefore attracted to the negatively charged hair surface and, because of their relatively low solubility and high molecular weight, are thermodynamically driven to leave the aqueous environment of the shampoo and deposit on the hair. These characteristics make cationic surfactants such as quaternary ammonium compounds particularly suited to the treatment of human hair. Thus, many hair conditioning products are based on quaternary ammonium compounds.

Such compounds can have one, two, or three long chain alkyl groups attached to the nitrogen head group. Typically, long chain alkyl groups comprise chain lengths of from about 12 to about 24 carbon atoms.

The ability to soften hair and reduce static charge build-up is typically a function of both the carbon atom chain length and the number of chains attached to the nitrogen head group. Generally, the longer the carbon chain and the greater the number of chains the greater the lubricity of the shampoo and static charge neutralization. However, the chance of the hair "matting" and acquiring a greasy and heavy look also increases.

Hair conditioners have often been separate from the shampoo. However, the desire by the consumer for the convenience of personal hair care products having both cleaning and conditioning functions in the same product has increased. Such products are known as 2-in-1 conditioning shampoos. These contain both cleaning and conditioning surfactants. Such conditioning shampoos clean soiled hair and leave a conditioner in the hair at the same time. Thus, it is unnecessary for the consumer to subsequently use a conditioner after using the shampoo.

However, cleaning surfactants are typically anionic, i.e., the surfactant activity resides in the negatively charged anion. Anionic and cationic surfactants are usually incompatible, forming a complex which precipitates from the solution when mixed. It is important that the correct surfactants be employed to prevent interference between the negatively charged cleaning surfactants and the positively charged conditioning surfactants.

One way of accomplishing this is to choose the cationic surfactant such that the positively charged quaternized nitrogen is sufficiently shielded from the negatively charged surfactants and raw materials present within the conditioning shampoo mix. This can be done by using trialkyl quaternary ammonium compounds. Such compounds are known in the art but are difficult to produce and require large amounts of energy and time. Moreover, they degrade relatively slowly in the environment.

What is needed is a formulation providing an effective biodegradable conditioner in a cleaning shampoo at minimal cost.

SUMMARY OF THE INVENTION

Hair conditioning compositions and 2-in-1 conditioning shampoos are provided herein which comprise:

a) a hair conditioning agent of the formula

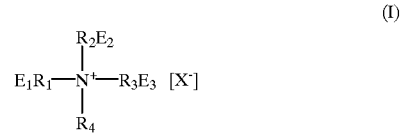

wherein $X^-$ is an anion, $R_1$, $R_2$, $R_3$ can be the same or different and are independently straight or branched chain alkyl groups of from 2 to about 6 carbon atoms; $R_4$ is a saturated or unsaturated, straight or branched chain aliphatic group having from about 1 to about 6 carbon atoms optionally substituted with hydroxy, epoxy or halogen and $E_1$, $E_2$ and $E_3$ can be the same or different at each occurrence and are selected from the group consisting of —H, —OH and aliphatic ester groups of the following formula (II):

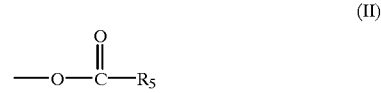

wherein $R_5$, is a saturated or unsaturated, straight or branched chain aliphatic group of from about 11 to about 24 carbon atoms, optionally substituted with hydroxy, epoxy or halogen, provided that at least one of $E_1$, $E_2$ or $E_3$ is a group of formula (II), the cationic surfactant being present in the composition at a concentration not exceeding about 4% by weight; and, b) an anionic surfactant or an anionic/nonionic surfactant combination.

The present formulations are superior to cleaning and conditioning shampoo compositions in which the conditioning surfactant is a trialkyl quaternary ammonium compound, and provides enhanced dry combing ability as well as reduced static charge build-up. Moreover, the hair conditioning agents of the present formulations may effectively be used in concentrations significantly below what was hitherto considered the minimum practicable amount.

DETAILED DESCRIPTION OF PREFERRED EMBODIMENTS

The hair conditioner and 2-in-1 and conditioning shampoos in accordance with this disclosure contain, inter alia, a cationic surfactant hair conditioning agent possessing aliphatic ester groups. The present formulations provide highly efficient use of the cationic surfactant for hair conditioning.

Generally, the conditioning shampoo formulation described herein contains an aqueous solution of one or more anionic surfactant, one or more cationic surfactant and, optionally, various builders and modifying ingredients.

The cationic surfactant employed as the hair conditioning agent in the present formulation possess the formula:

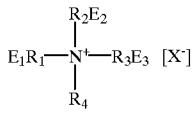

wherein: $X^-$ is an anion e.g., selected from chloride, bromide, iodide, nitrate, nitrite, methylsulfate, ethylsulfate, methyl phosphate, acetate, etc.; $R_1$, $R_2$ and $R_3$ can be the same or different and are independently straight or branched chain alkyl groups of from about 2 to about 6 carbon atoms e.g., ethyl, propyl, isopropyl, butyl, sec-butyl, tert-butyl, pentyl, methylpentyl, hexyl, etc.; $R_4$ is a saturated or unsaturated, straight or branched chain aliphatic group having from 1 to about 6 carbon atoms optionally substituted with hydroxy, epoxy, or halogen; and $E_1$, $E_2$ and $E_3$ can be the same or different at each occurrence and are selected from the group consisting of —H, —OH, and aliphatic ester groups of the formula (II):

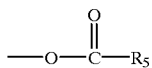

wherein $R_5$ is a saturated or unsaturated, straight or branched chain aliphatic group of from about 11 to about 24 carbon atoms, optionally substituted with hydroxy, epoxy, or halogen, provided that at least one of $E_1$, $E_2$, or $E_3$ is a group of formula (II).

The foregoing cationic surfactant, a quaternary ammonium compound, is advantageously prepared by reacting a trialkanol amine with a fatty acid or fatty acid ester to provide an esteramine and thereafter reacting the esteramine with an alkylating agent to provide the quaternary ammonium compound.

The alkanol amine is typically chosen from a group of alkanol amines such that there is one hydroxyl function per alkyl group attached to the nitrogen. Thus, the alkanol amine contains three hydroxyl functions per molecule. Suitable alkanol amines include triethanol amine ("TEA"), diethanol isopropanol amine, ethanol diisopropanol amine, diethanol butanol amine, ethanol dibutanol amine, triisopropanol amine, ethanol di-n-propanol amine, diethanol n-propanol amine, and the like.

The aliphatic chain of the fatty acid/ester reactions) can range in length from about 11 to about 24 carbon atoms and can be straight or branched. The aliphatic chains can be fully saturated or they can contain some unsaturation. While unsaturation may lead to some improvement in performance properties and formulation benefits, unsaturated molecules may also have a tendency to oxidize, thereby affecting color and odor stability of the shampoo composition. However, the stability of compositions containing unsaturated components can be improved by careful manufacturing techniques and by the use of stabilizers such as antioxidants (e.g., BHT) and sequesterants (e.g., EDTA) in the raw materials, products, cationic surfactants and/or final formulation. Although it is not necessary for all three aliphatic chains to be identical, such is advantageous since identical aliphatic chains may more readily achieve compatibility of the cationic surfactant component with other components of the final shampoo/conditioner formulation. Suitable fatty acid/ester reactant(s) for preparing the intermediate esteramine herein include stearic acid, lauric acid, oleic acid, myristic acid, behenic acid, erucic acid, palmitic acid, linoleic acid and lower alkyl esters of these fatty acids, and mixtures thereof. The fatty acids can be a mixture of fatty acids such as those derived from tallow, soy, palm, canola, rapeseed, coconut, or other natural sources.

The reaction between the alkanol amine and the fatty acid/ester is carried out in the presence of an acid catalyst such as hypophosphorous acid at a molar ratio of fatty acid/ester to alkanol amine of from about 1.5:1 to about 3.0:1, preferably about 2.4:1 to about 3.0:1 and most preferably about 2.8:1 to about 3.0:1.

Preferably, $R_1$, $R_2$ and $R_3$ are each —$(CH_2)_2$—, $R_5$ is $C_{15}$ alkyl, and $X^-$ is methyl sulfate. This preferred cationic surfactant can be produced by the reaction of a $C_{16}$ fatty acid and triethanolamine ("TEA") at a fatty acid to TEA ratio of preferably about 3:1. The resulting esteramine is then reacted with dimethyl sulfate to form the quaternary ammonium salt.

The foregoing reaction conditions will produce a reaction product containing a mixture of monoester, diester and triester cationic surfactant components. Particularly useful cationic surfactant compositions contain greater than about 50 percent by weight of the triester compound, preferably greater than about 60 percent and most preferably greater than about 75 percent of the triester. The diester content can be less than about 30 percent by weight of the reaction product, preferably less than about 25 percent, and most preferably less than about 20 percent by weight of the reaction product. Monoester can constitute less than about 7 percent by weight of the reaction product. Preferably, the reaction product contains less than about 5 percent monoester, and most preferably monoester constitutes less than about 3 weight percent of the reaction product.

Surprisingly, the cationic surfactant in the conditioning shampoo formulation is effective at a concentration not exceeding 4% by weight of the formulation, preferably not exceeding 3% by weight of the formulation and more preferably not exceeding 2% by weight of the formulation.

As mentioned above, the conditioning shampoo formulation of the present invention includes an anionic surfactant. Suitable anionic surfactants which provide a cleansing function in the present formulation include ammonium lauryl sulfate, ammonium laureth sulfate, sodium lauryl sulfate, and sodium laureth sulfate. Ammonium lauryl sulfate is preferred. It is also contemplated that a mixture of anionic and nonionic surfactants can be employed in formulating the present conditioning shampoos. Suitable nonionic surfactants are disclosed in U.S. Pat. No. 3,632,396, the disclosure of which is incorporated herein by reference.

The shampoo and conditioner formulation can optionally also include inorganic builders such as sodium phosphate and disodium phosphate; viscosity control agents such as sodium chloride; hydrotopes such as ammonium, sodium, or potassium salts of xylene or cumene sulfonates to increase the solubility of less soluble ingredients; chelating agent such as sodium salts of ethylene diamine tetraacetic acid ("EDTA"), particularly disodium EDTA; foaming boosters such as cocamide MEA, cocamide DEA, soyamide DEA, lauramide DEA, oleamide MIPA, stearamide MEA, myristamide MEA, lauramide MEA, capramide DEA, ricinolamide DEA, myristamide DEA, stearamide DEA, oleylamide DEA, tallowamide DEA, lauramide MIPA, tallowamide MEA, isostearamide DEA, isostearamide MEA, and combinations thereof; preservatives such as 5-chloro-2-methyl-4-isothiazolin-3-one and 2-methyl-4-isothiazolin-3-one (available as a mixture under the designation KATHON®); fatty alcohol components such as cetyl and stearyl alcohols; silicone conditioners such as dimethicone; and fragrance.

Additionally, other optional components can be added to the conditioning shampoo composition of the present invention as long as the basic properties of the composition are not adversely affected. Such optional components can include non-ionic surfactants such as ethers of polyols and sugars, fatty acid alkanolamides, polyethylene glycols, ethoxylated or propoxylated alkylphenols, ethoxylated or propoxylated fatty alcohols and condensation products of ethylene oxide with long chain amides; amphoteric surfactants such as cocoamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate; dyes and hair colorants; opacifiers and pearlescing agents such as those disclosed and described in U.S. Pat. No. 5,384,114; medications including antidandruff agents such as salicylic acid, elemental sulfur, selenium sulfide, zinc pyrithione, 1-hydroxypyridone and undecylenic acid; acids; alkalies; buffers; water softeners; thickeners, and the like.

EXAMPLE I

A cationic surfactant for use in the present conditioning shampoo is prepared as follows:

In a first step, 428 grams (1.67 moles) of molten palmitic acid, 0.42 grams of BHT, 0.42 grams of BHA, and 0.75 grams of a 50% solution of hypophosphorous acid were charged to a reaction vessel which was connected to an overhead stirrer, three ball Snyder column, addition funnel, distillation equipment, nitrogen sparge, and a temperature control. The mixture was kept at about 70° C. under nitrogen and 90.6 grams (0.61 moles) of triethanolamine (TEA) was added. After TEA addition, the temperature of the reaction mixture was gradually increased at the rate of about 1.7° C. per minute. When the temperature reached 105° C., vacuum was applied to bring the system pressure down to 26" Hg. The heating was continued until the temperature was raised to about 195° C. The mixture was held at this temperature and pressure until a desired level of diesteramine and triesteramine was produced.

In a second step, a reaction vessel was fitted with temperature control, stirrer, condenser, nitrogen sweep and an addition funnel. 425 grams (0.52 moles) of the esteramine from step 1 was added to the reaction vessel along with 48.5 grams of isopropanol. This mixture was heated to about 55° C. under nitrogen. 61.7 grams (0.49 moles) of dimethyl sulfate was added dropwise at such a rate that the temperature did not exceed 85° C. The reaction was continued for two hours. Then 0.34 grams of 40% solution of EDTA and 18.5 grams isopropanol were added. In this manner a trialkyl methyl quaternary compound is produced.

EXAMPLE II

A composition of conditioning shampoo is formulated using the cationic surfactant of Example I as follows:

A first blending component is formed by mixing 45 parts water, 38 parts of 30% ammonium lauryl sulfate solution, and 2 parts of ammonium xylene sulfonate and heating the mixture to about 70° C. for a period of time to insure adequate blending.

A second blending component is separately formed by mixing 2 parts cocamide MEA, 2 parts cetyl alcohol, 1 part stearyl alcohol, 2 parts dimethicone, and 1.8 parts of the preferred cationic surfactant mentioned above. The mixture is heated to a temperature sufficient to liquify the ingredients and the second blending component is then added to the first blending component with moderate agitation.

A third blending component is separately produced by heating 5 parts of water to 50° C. and adding thereto 0.2 parts disodium phosphate, 0.3 parts sodium phosphate, 0.01 parts disodium EDTA and 0.2 parts sodium chloride. The ingredients of the third blending component are mixed with agitation until dissolved. Then the third blending component is added to the mixture of the first and second blending components. With continued agitation the combined blending components are cooled to below 40° C. to form the conditioning shampoo. Optionally, preservatives and fragrance may be added as desired.

The cationic surfactant disclosed herein provides superior hair conditioning results as compared with prior alkyl quaternary ammonium surfactants such as tricetyl methyl ammonium chloride (currently available from AKZO Nobel, Inc., of Dobbs Ferry, N.Y. under the designation Arquad® 316) even at concentrations below 2%. For example, as compared with a shampoo containing Arquad® 316 conditioner in the same percentage, the preferred shampoo composition set forth above with the preferred cationic surfactant provides superior dry combing ability along with about a 10% to 15% voltage reduction in static charge buildup.

While the above description contains many specifics, these specifics should not be construed as limitations on the scope of the invention, but merely as exemplifications of preferred embodiments thereof. Those skilled ion the art will envision many other possible variations that are within the scope and spirit of the invention as defined by the claims appended hereto.

What is claimed is:

1. A method of making a 2-in-1 hair conditioning agent comprising the steps of:

a) reacting an alkanolamine with a fatty compound to form a reaction product, the fatty compound having an aliphatic group of from about 11 to about 24 carbon atoms and being selected from the group consisting of fatty acid and fatty acid ester, wherein the molar ratio of fatty compound to alkanolamine is in the range from about 1.5:1 to about 3.0:1;

b) reacting the reaction product of step a) with an alkylating agent to form a reaction product containing mono-, di- and tri-esteramines, at least about 50 percent by weight of the total weight of the reaction product being triesteramine; and c) incorporating the reaction product of step b) into an anionic surfactant system to produce a 2-in-1 conditioning shampoo.

2. The method of claim 1 wherein the molar ratio of fatty compound to alkanolamine ranges from about 2.4:1 to about 3.0:1.

3. The method of claim 1 wherein the molar ratio of fatty compound to alkanolamine ranges from about 2.8:1 to about 3.0:1.

4. The method of claim 1 wherein the step of reacting the alkanolamine with the fatty compound is performed by heating a mixture of the alkanolamine and fatty compound in the presence of hypophosphorous acid.

5. The method of claim 1 wherein the alkanolamine is triethanolamine, the fatty compound is palmitic acid, and the alkylating agent is dimethyl sulfate.

6. A method for making a hair conditioning agent containing at least one compound of the formula (I):

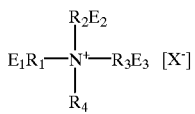
(I)

wherein: X is an anion; $R_1$, $R_2$, and $R_3$, can be the same or different and are independently straight or branched chain alkylene groups of from 2 to about 6 carbon atoms, R4 is a saturated or unsaturated, straight or branched chain aliphatic group of from 1 to about 6 carbon atoms optionally substituted with hydroxy, epoxy, or halogen; and $E_1$, $E_2$ and $E_3$ can be the same or different at each occurrence and are selected from the group consisting of —H, —OH and aliphatic ester groups of the following formula (II):

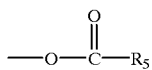
(II)

wherein $R_5$ is a saturated or unsaturated, straight or branched chain aliphatic group of from about 11 to about 24 carbon atoms optionally substituted with a hydroxy, epoxy, or halogen, the method comprising the steps of:

a) reacting a trialkanolamine with a fatty compound to form a reaction product, the fatty compound having an aliphatic group of from about 11 to about 24 carbon atoms and being selected from the group consisting of fatty acids and fatty acid esters, wherein the molar ratio of fatty compound to trialkanolamine is in the range from about 1.5:1 to about 3.0:1; and b) reacting the reaction product of step a) with an alkylating agent to form a reaction product containing mono, di-, and tri-esteramines, at least about 50 percent by weight of the reaction product being triesteramine.

7. The method of claim 6 wherein the molar ratio of fatty compound to trialkanolamine ranges from about 2.4:1 to 3.0:1.

8. The method of claim 6 wherein the molar ratio of fatty compound to trialkanolamine ranges from about 2.8:1 to 3.0:1.

9. The method of claim 6 wherein the step of reacting the alkanolamine with the fatty compound is performed by heating a mixture of trialkanolamine and fatty compound in the presence of hypophosphorous acid.

10. The method of claim 6 wherein the trialkanolamine is triethanolamine, the fatty compound is palmitic acid and the alkylating agent is dimethyl sulfate.

* * * * *